United States Patent [19]

Shibata et al.

[11] 4,024,000
[45] May 17, 1977

[54] STABILIZATION OF β-AMYLASE IN AQUEOUS MEDIUM

[75] Inventors: Osamu Shibata; Hitoshi Taniguchi, both of Sennan, Japan

[73] Assignee: Fuji Oil Company Ltd., Osaka, Japan

[22] Filed: Aug. 12, 1975

[21] Appl. No.: 603,811

[30] Foreign Application Priority Data

Aug. 13, 1974 Japan .............................. 49-93046

[52] U.S. Cl. .............................. 195/63; 195/66 R; 195/68
[51] Int. Cl.² ......................................... C07G 7/02
[58] Field of Search .................. 195/66 R, 63, 68

[56] References Cited

UNITED STATES PATENTS

| | | | |
|---|---|---|---|
| 3,524,798 | 8/1970 | Lloyd et al. | 195/63 |
| 3,634,266 | 1/1972 | Theile et al. | 195/63 X |
| 3,720,583 | 3/1973 | Fisher | 195/31 R |
| 3,769,168 | 10/1973 | Masuda | 195/66 R |
| 3,804,718 | 4/1974 | Okada et al. | 195/66 R |

OTHER PUBLICATIONS

Michaels, "Ultrafiltration", Booklet No. 905, Amicon Corporation, Mar. 1968, p. 10.

*Primary Examiner*—Lionel M. Shapiro
*Attorney, Agent, or Firm*—Birch, Stewart, Kolasch & Birch

[57] ABSTRACT

An aqueous solution containing β-amylase obtained by extraction of β-amylase-containing plants with water or a buffer solution can be efficiently concentrated and purified at a high temperature by membrane separation without inactivation of β-amylase and putrefaction of the aqueous solution by incorporating a divalent or trivalent metal ion into the aqueous solution and adjusting the pH of the aqueous solution to about 4.5 to 8.0.

20 Claims, No Drawings

STABILIZATION OF β-AMYLASE IN AQUEOUS MEDIUM

The present invention relates to the stabilization of β-amylase in an aqueous medium. More particularly, it relates to a method for concentration and purification of an aqueous solution containing β-amylase under the stabilized condition.

β-Amylase is one of the important enzymes nowadays which is widely used in various industries such as the fermentation and food industries. In particular, the recent development of the production of high purity maltose from β-amylase has resulted in an abrupt increase in the demand for β-amylase.

As is well known, β-amylase is present in various plants such as barley, wheat, malt, sweet potato and soy bean as well as Bacilli and, therefore, is obtained from them by extraction with water or a buffer solution. Since, however, the extract usually contains a large amount of soluble organic materials such as saccharides and protein decomposition products in addition to β-amylase, it is apt to be putrefied. Thus, further treatment of the extract for enhancing the concentration and purity of β-amylase at a relatively high temperature over about 45° C results frequently in putrefaction during the operation. In addition, such high temperature causes the inactivation of β-amylase, which is quite unstable to heat. When the treatment is carried out at a relatively low temperature from about 20° to 30° C, the putrefaction and inactivation as mentioned above can be avoided. But, in such case, the efficiency of the concentration and purification of β-amylase is considerably decreased.

As the result of an extensive study, it has now been found that β-amylase in an aqueous medium can be stabilized even at a high temperature (e.g. about 40° to 55° C) when a divalent or trivalent metal ion is present therein and the pH is adjusted to about 4.5 to 8.0. It has also been found that the presence of the said metal ion at such pH is effective in prevention of the putrefaction of an aqueous extract containing β-amylase. The present invention is based on these findings.

Accordingly, a basic object of the present invention is to embody a stabilized aqueous solution of β-amylase. Another object of this invention is to embody a method for stabilization of β-amylase in an aqueous medium. A further object of the invention is to embody a method for concentration and purification of an aqueous solution containing β-amylase under the stabilized condition without putrefaction. These and other objects will be apparent to those skilled in the art to which this invention pertains from the foregoing and subsequent descriptions.

According to the present invention, there is provided a stabilized aqueous solution of β-amylase which comprises a divalent or trivalent metal ion and is adjusted at a pH of about 4.5 to 8.0.

The aqueous β-anylase solution to be stabilized by the invention may be any aqueous solution containing β-amylase. From the practical viewpoint, it may be an extract of β-amylase-containing plants such as barley, wheat, malt, sweet potato and soy bean with water or a buffer solution having a pH at which β-amylase is stable (e.g. about pH 4 to 10). It may also be a juice obtained by squeezing the said plants. Further, it may be an extract of Bacilli containing β-amylase with water or a buffer solution. One of the typical procedures for obtaining the aqueous β-amylase solution comprises extracting crushed soy bean with a buffer solution of pH 4.5 to 5.5, or extracting defatted soy bean with a neutral or a weakly alkaline aqueous solution and adjusting the resulting extract to an isoelectric point for separation and removal of the protein curd therefrom. Another typical procedure comprises crushing sweet potato together with water and removing solid materials from the crushed material.

In order to obtain a β-amylase product of high purity, it is preferred to eliminate previously materials of low solubility in the stable region of β-amylase. Typical examples of such materials are proteins having an isoelectric point at pH 4 to 6, which may be eliminated by conventional procedures such as precipitation with acids, salting out at low saturation degrees and addition of alkaline earth metal salts.

To the aqueous β-amylase solution thus obtained, a divalent or trivalent metal compound which can liberate a divalent or trivalent metal ion in an aqueous medium is added. Examples of the metal compound are hydroxides of calcium, magnesium, barium, aluminum, etc. Salts of these metals with acids such as hydrochloric acid, phosphoric acid, lactic acid, citric acid and tartaric acid are also utilizable. The metal compound is incorporated in an amount to make a concentration of not less than about 0.01% by weight to not more than about 5% by weight, preferably of not less than about 0.1% by weight to not more than 1% by weight in the aqueous β-amylase solution.

The pH of the resulting aqueous β-amylase solution is adjusted to a pH of about 4.5 to 8.0, preferably of about 5.0 to 7.0. Within the said range, a lower pH is more effective in prevention of putrefaction.

The resultant aqueous β-amylase solution incorporated with the said metal compound and adjusted to the said pH is quite stable to heat and can be subjected to chemical and/or physical treatment at a relatively high temperature (e.g. about 45° to 55° C) for a comparatively long period of time without any substantial inactivation and putrefaction.

Among various treatments to which the stabilized aqueous β-amylase solution may be subjected, the most advantageous one is membrane separation.

The term "membrane separation" as herein used is intended to mean a conventional procedure for separation of water and low molecular weight materials from high molecular weight materials by the utilization of the selective permeability of a membrane so as to enhance the concentration of the high molecular materials with elevation of their purity.

In addition to the stabilization and putrefaction preventing effects as explained above, the presence of the divalent or tivalent metal ion is surprisingly effective in improvement of the permeation efficiency and enhancing the effect in salting out.

The concentration and purification of conventional aqueous β-amylase solutions by membrane separation has been carried out at a relatively low temperature (e.g. below about 25° C) in order to avoid the inactivation and putrefaction. Since the permeation ability of a membrane is generally increased with a higher temperature, the said low temperature results in the decrease of the efficiency of membrane separation.

For the stabilized aqueous β-amylase solution of the invention, membrane separation is applicable at a high temperature (e.g. 45° to 55° C), and thus the purpose of the concentration and purification of β-amylase can be achieved efficiently.

The membrane to be used for membrane separation may be any conventional one to be employed in ultrafiltration, reverse osmosis or the like. Such membrane may be made of cellulose acetate, aromatic polyamides, etc. Specific examples are membranes of the HFA series and of the AS-100 series manufactured by ABCOR Company, U.S.A.

The membrane separation may be carried out in a conventional manner, usually at a temperature of about 45° to 55° C (preferably about 47° to 52° C) under an elevated pressure. In general, a higher pressure is better insofar as the membrane is tolerable. When, for instance, the membrane separation is ultrafiltration with a HFA-180 membrane, the operation pressure may be from about 3.5 to 4.2 kg/cm$^2$. Further, for instance, the reverse osmosis with a AS-197 membrane may require an operation pressure of about 50 to 60 kg/cm$^2$.

The concentrated and purified β-amylase solution obtained by the membrane separation may be, if necessary, salted out by addition of an appropriate salt such as ammonium sulfate or sodium chloride to precipitate a fraction containing β-amylase. Collection of the precipitate and drying affords a β-amylase product of high purity.

Practical and presently preferred embodiments of the invention are illustratively shown in the following Examples.

EXAMPLE 1

To soy bean whey (80 liters) by-produced in the production of soy bean protein, a solution of calcium chloride (160 g) in water (150 g) was added. The resulting mixture was adjusted to pH 5.0 and then concentrated at 50° C by ultrafiltration using a membrane HFA-180 (manufactured by ABCOR Company, U.S.A.) until the total volume became 8 liters. In the same manner, soy bean whey to which calcium chloride was not added was subjected to ultrfiltration at 25°, 40° and 50° C.

The results are shown in Table 1.

Table 1

| | CaCl$_2$ | Temperature (° C) | β-Amylase activity (A) before concentration (units/ml) | β-Amylase activity (B) after concentration (units/ml) | Time (C) required for concentration (hours) | Concentration efficiency $\frac{B}{10A \times C} \times 100$ (%) |
|---|---|---|---|---|---|---|
| Example 1 | Added | 50 | 140 | 1232 | 5¾ | 15.6 |
| Comparative Example 1 | not added | 50 | 140 | 648 | 6 | 7.7 |
| Comparative Example 2 | not added | 25 | 178 | 1820 | 10½ | 10.3 |
| Comparative Example 3 | not added | 40 | 178 | 343 | 8 | 2.4 |

Note: In Comparative Example 3, putrefaction was observed.

EXAMPLE 2

Sweet potato juice after separation of starch therefrom was adjusted with hydrochloric acid to pH 5.2, and coagulated proteins and other impurities were removed to give a solution having a β-amylase activity of 300 units/ml. The solution (100 liters) was adjusted to pH 5.5, and a solution of aluminum chloride (200 g) in water (200 g) was added thereto. The resulting mixture of pH 6.8 was concentrated at 50° C by ultrafiltration using a membrane HFA-180 (manufactured by ABCOR Company) until the total volume became 10 liters. The β-amylase activity of the concentrated solution was 2700 units/ml.

EXAMPLE 3

Crushed soy bean was extracted with an acetate buffer of pH 5.4, and insoluble materials were removed to give a solution having a β-amylase activity of 160 units/ml. To the solution (80 liters), there was added calcium hydroxide (200 g), and the pH was adjusted to 6.6. The resulting mixture was concentrated at 50° C by reverse osmosis using a membrane AS-197 (manufactured by ABCOR Company) until the total volume became 8 liters. The time required for concentration was 5 hours. No putrefaction was observed. The β-amylase activity of the concentrated solution was 1460 units/ml.

EXAMPLE 4

To soy bean whey by-produced in the production of soy bean protein, magnesium chloride was added to make a concentration of 0.25 % by weight. The resulting solution was adjusted to pH 6.0 at 48° C and concentrated by about 10 fold by a stage-in-series membrane concentration machine using a membrane HFA-180 (manufactured by ABCOR Company). While the β-amylase activity before concentration was 150 units/ml, that after concentration was 1300 units/ml.

What is claimed is:

1. A method for stabilization of an aqueous solution of β-amylase which comprises incorporating a divalent or trivalent metal compound selected from the group consisting of the hydroxides of calcium, magnesium, barium and aluminum and salts thereof with acids into the aqueous solution in a concentration of not less than about 0.01% by weight and adjusting the pH of the aqueous solution to about 4.5 to 8.0.

2. The method according to claim 1, wherein the concentration of the divalent or trivalent metal compound is not less than about 0.1% by weight.

3. The method according to claim 1, wherein the pH is adjusted to about 5.0 to 7.0.

4. The method according to claim 1, wherein the aqueous solution is an extract obtained by extraction of barley, wheat, malt, sweet potato, soy bean or Bacilli with water or a buffer solution.

5. The method according to claim 4, wherein the aqueous solution is soy bean whey.

6. A method for concentration and purification of an aqueous solution containing β-amylase by subjecting the same to membrane separation, wherein the aqueous solution comprises a divalent or trivalent metal compound selected from the group consisting of the hydroxides of calcium, magnesium, barium and aluminum and salts thereof with acids in a concentration of not less than about 0.01% by weight, said solution having a pH of about 4.5 to 8.0, and the membrane separation is carried out at a temperature of about 45° to 55° C.

7. The method according to claim 6, wherein the membrane separation comprises ultrafiltration.

8. The method according to claim 6, wherein the membrane separation comprises reverse osmosis.

9. A method for preparation of an aqueous solution containing β-amylase at a high concentration and a high purity, which comprises subjecting a β-amylase-containing extract obtained by treatment of a β-amylase-containing material with water or a buffer solution to membrane separation at a temperature of about 45° to 55° C., the said extract having incorporated therein a divalent or trivalent metal compound selected from the group consisting of the hydroxides of calcium, magnesium, barium and aluminum and salts thereof with acids in a concentration of not less than about 0.01% by weight and the pH of said extract being about 4.5 to 8.0.

10. The method according to claim 9, wherein the β-amylase-containing material is barley, wheat, malt, sweet potato, soy bean or Bacilli.

11. A stabilized aqueous solution of β-amylase which comprises a divalent or trivalent metal compound selected from the group consisting of the hydroxides of calcium, magnesium, barium and aluminum and salts thereof with acids in a concentration of not less than about 0.01% by weight, said solution having a pH of about 4.5 to 8.0.

12. The method according to claim 1, wherein the metal compound is a salt of an acid selected from the group consisting of hydrochloric acid, phosphoric acid, lactic acid, citric acid and tartaric acid.

13. The method according to claim 1, wherein the concentration of metal compound in said aqueous soluton is about 0.01% to about 5% by weight.

14. The method according to claim 1, wherein the concentration of metal compound in said aqueous solution is about 0.1% to about 1% by weight.

15. The method according to claim 9, wherein the metal compound is a salt of an acid selected from the group consisting of hydrochloric acid, phosphoric acid, lactic acid, citric acid and tartaric acid.

16. The method according to claim 9, wherein the concentration of metal compound in said aqueous solution is about 0.01% to about 5% by weight.

17. The method according to claim 9, wherein the concentration of metal compound in said aqueous solution is about 0.1% to about 1% by weight.

18. The stabilized aqueous solution of β-amylase according to claim 11, wherein the metal compound is a salt of an acid selected from the group consisting of hydrochloric acid, phosphoric acid, lactic acid, citric acid and tartaric acid.

19. The stabilized aqueous solution of β-amylase according to claim 11, wherein the concentration of metal compound in said aqueous solution is about 0.01% to about 5% by weight.

20. The stabilized aqueous solution of β-amylase according to claim 11, wherein the concentration of metal compound in said aqueous solution is about 0.1% to about 1% by weight.

* * * * *